(12) United States Patent
Schottenberger et al.

(10) Patent No.: US 6,239,299 B1
(45) Date of Patent: May 29, 2001

(54) METALLOCENES WITH FERROCENYL-SUBSTITUTED BRIDGES USED IN OLEFIN POLYMERIZATION

(75) Inventors: Herwig Schottenberger, Patsch; Ingo Wartusch, Telfs im Stubai; Eberhard Ernst, Katsdorf; Jens Reussner, Gramastetten, all of (AT)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 09/509,214

(22) PCT Filed: Oct. 1, 1998

(86) PCT No.: PCT/EP98/06268

§ 371 Date: Mar. 24, 2000

§ 102(e) Date: Mar. 24, 2000

(87) PCT Pub. No.: WO99/19337

PCT Pub. Date: Apr. 22, 1999

(30) Foreign Application Priority Data

Oct. 9, 1997 (AT) .................................................... 1710/97

(51) Int. Cl.[7] ............................. C07F 17/00; C08F 10/00
(52) U.S. Cl. ................................. 556/28; 556/11; 556/12; 556/43; 556/53; 556/143; 556/144; 526/114; 526/115; 526/117; 526/348; 526/351; 526/352; 526/943
(58) Field of Search .................................. 556/11, 12, 28, 556/43, 53, 143, 144; 502/114; 526/115, 117, 348, 351, 352, 943

(56) References Cited

U.S. PATENT DOCUMENTS

| 5,455,365 | 10/1995 | Winter et al. ............................. 556/7 |
| 5,521,265 | 5/1996 | Schottenberger et al. ............ 526/115 |

FOREIGN PATENT DOCUMENTS

| 0 376 154 | 7/1990 | (EP) . |
| 0 659 757 | 6/1995 | (EP) . |
| 0 664 304 | 7/1995 | (EP) . |
| 0 745 606 | 12/1996 | (EP) . |
| 0 754 698 | 1/1997 | (EP) . |
| 96/22995 | 8/1996 | (WO) . |

OTHER PUBLICATIONS

M. Mitani et al., *Bull. Chem. Soc. Jpn.,* 69(10), 2967–2976 (1996).
Mitani et al., Chemistry Letters, pp. 905–906 (1995).
Mitani et al., Bull. Chem. Soc. Jpn., 69, pp. 2967–2796 (1996).
Atzkern et al., J. Am. Chem. Soc., 117, pp. 997–1011 (1995).
Chemical Abstracts, 125:59215b (1996).
Chemical Abstracts, 124:290568j (1996).
Chemical Abstracts, 127:18084f (1997).

*Primary Examiner*—Porfirio Nazario-Gonzalez
(74) *Attorney, Agent, or Firm*—Wenderoth, Lind & Ponack, L.L.P.

(57) ABSTRACT

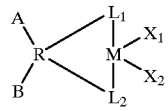

The invention relates to metallocenes of formula (I), in which M is a metal from the Ti, Zr, Hf, V, Nb, Ta group or an element from the lanthanide group, $X_1$ and $X_2$ stand for an alkyl-, aryl-, alkenyl-, arylalkyl-, alkylaryl- or arylalkenyl group and $L_1$ and $L_2$ are hydrocarbon capable of forming a sandwich structure with M. R stands for C, Si, Ge or Sn, A and B are ferrocenyl-substituted radicals, or B is optionally a radical $X_1$ of $X_2$. The metallocenes are preferably used as catalysts in the polymerization of olefins.

9 Claims, No Drawings

METALLOCENES WITH FERROCENYL-SUBSTITUTED BRIDGES USED IN OLEFIN POLYMERIZATION

The invention relates to new metallocenes and their use as catalysts in olefin polymerization.

Metallocenes of the metals of transition group IV of the Periodic Table of the Elements are highly active catalysts for the polymerization of olefins. The resulting polyolefins have new property combinations and supplement the product range of the polyolefins prepared hitherto using known conventional Ziegler-Natta catalysts.

It is known that catalysts based on unbridged, substituted and unsubstituted biscyclopentadienyl metallocenes in combination with aluminoxanes as cocatalyst can be used for the preparation of polyethylene and ethylene-α-olefin copolymers (EP-B 128 046). It is also known that stereoregular polyolefins can be prepared using bridged, chiral metallocenes. For bridging the ligand systems, use is mostly made of dimethylsilanediyl groups (EP-A 485 823), methylphenylsilanediyl groups (EP-A 376 154), ethylene groups (Brintzinger et al., J. Organomet. Chem., 288 (1985) 63–67) and isopropylidene bridges (EP-A 351 391). Depending on the ligand type and the substituents, isotactic, syndiotactic, hemiisotactic, stereoblock-type and atactic homopolymers and copolymers having aliphatic or cyclic structures can be prepared. As ligands, preference is given to using substituted and unsubstituted cyclopentadienyl units (EP-A 316 155), substituted and unsubstituted indenyl units (Hoechst EP-A 485 823) and also substituted and unsubstituted cyclopentadienyl units in combination with unsubstituted fluorenyl groups (EP-A 351 391). Likewise, it is known that bridged metallocenes having a cyclopentadienyl system and a heteroatom ligand (constrained geometry catalyst) can also be used for the polymerization of olefins (U.S. Pat. No. 5,096,867).

Among these various types of metallocene, the bridged, chiral, substituted bisindenyl systems have attained particular importance. Thus, it was able to be shown that the type of substituents and the position of the substituents on the ligand of the metallocene have a significant influence on the reactivity of the catalyst system and the stereoregular structure of the polyolefins obtained. In addition, for targeted influencing of the polyolefin properties via the structure of the metallocenes, precise matching of the effects of ligands and bridge is desirable.

It is therefore an object of the invention to find further structural variants of bridged metallocenes as catalysts for the polymerization of olefins which give polyolefins, in particular polypropylenes, having relatively high molar masses and, at the same time, a narrow molar mass distribution.

It has now surprisingly been found that ferrocenyl-substituted, silanediyl-bridged metallocene systems are suitable catalysts for the preparation of polyolefins and in particular of polypropylenes having gradated properties.

The present invention accordingly provides metallocenes of the formula I

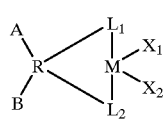

(I)

where M is a metal selected from the group consisting of Ti, Zr, Hf, V, Nb and Ta or an element selected from the group consisting of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, hydrogen or a halogen atom, $L_1$ and $L_2$ a) are identical or different and are each an unsubstituted, monosubstituted or polysubstituted monocyclic or polycyclic hydrocarbon radical containing at least one cyclopentadienyl unit which can form a sandwich structure with M, or b) $L_1$ is an unsubstituted, monosubstituted or polysubstituted monocyclic or polycyclic hydrocarbon radical containing at least one cyclopentadienyl unit which can form a sandwich structure with M, and $L_2$ is an amido, phosphido or arsenido radical of the formula

where D is nitrogen, phosphorus or arsenic and E is as defined for $X_1$ and $X_2$, R is carbon, silicon, germanium or tin, A and B are identical or different and are ferrocenyl-substituted radicals of the formula

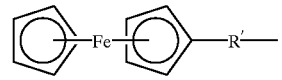

where R' is a $C_1$–$C_{10}$-alkyl group or a $C_6$–$C_{10}$-aryl group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, where B may also be as defined for $X_1$ or $X_2$.

Preferred radicals A and B are ferrocenylalkyl radicals, particularly preferably ferrocenylethyl radicals.

Preferred ligands $L_1$ and/or $L_2$ are substituted or unsubstituted cyclopentadienyl, indenyl or fluorenyl radicals. Particular preference is given to cyclopentadienyl, tetramethylcyclopentadienyl, indenyl, 2-methylindenyl, 2-methyl-4,5-benzindenyl, 2-methyl-4-arylindenyl and fluorenyl units and also ferrocene- and ruthenocene-substituted units as are described, for example, in EP-A-673 946.

According to the invention, the following metallocenes are particularly preferred:

bis(ferrocenylethyl)silanediyldicyclopentadienylzirconium dichloride, bis(ferrocenylethyl)silanediyldiindenylzirconium dichloride, bis(ferrocenylethyl)silanediylbis(2-methylindenyl)-zirconium dichloride, bis(ferrocenylethyl)silanediylbis(2-methyl-4,5-benzindenyl)zirconium dichloride, bis(ferrocenylethyl)silanediylbis(2-methyl-4-phenylindenyl)zirconium dichloride, bis(ferrocenylethyl)silanediylbis(2-methyl-4-naphthylindenyl)zirconium dichloride, bis(ferrocenylethyl)silanediyldifluorenylzirconium dichloride, bis(ferrocenylethyl)silanediyl(fluorenyl)(cyclopentadienyl)zirconium dichloride, bis(ferrocenylethyl)silanediyl(fluorenyl)(indenyl)-zirconium dichloride, bis(ferrocenylethyl)silanediyl(tetramethylcyclopentadienyl)(indenyl)zirconium dichloride,
methyl(ferrocenylethyl)silanediyldicyclopentadienylzirconium dichloride,
methyl(ferrocenylethyl)silanediyldiindenylzirconium dichloride,
methyl(ferrocenylethyl)silanediylbis(2-methylindenyl)zirconium dichloride,
methyl(ferrocenylethyl)silanediylbis(2-methyl-4,5-benzindenyl)zirconium dichloride,
methyl(ferrocenylethyl)silanediylbis(2-methyl-4-phenylindenyl)zirconium dichloride,
methyl(ferrocenylethyl)silanediylbis(2-methyl-4-naphthylindenyl)zirconium dichloride,
methyl(ferrocenylethyl)silanediyldifluorenylzirconium dichloride,
methyl(ferrocenylethyl)silanediyl(fluorenyl)(cyclopentadienyl)zirconium dichloride,
methyl(ferrocenylethyl)silanediyl(fluorenyl)(indenyl)zirconium dichloride and
methyl(ferrocenylethyl)silanediyl(tetramethylcyclopentadienyl)(indenyl)zirconium dichloride.

The invention further provides a process for preparing the metallocenes I, which comprises reacting a compound of the formula II

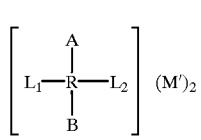  (II)

where $L_1$, $L_2$, A, B and R are as defined for formula I and M' is an alkali metal, preferably lithium, with a compound of the formula III $M(X')_2X_1X_2$  (III), where M, $X_1$ and $X_2$ are as defined for formula I and X' is a halogen atom, preferably chlorine. The metallocenes I can be prepared, for example, according to the following reaction scheme:

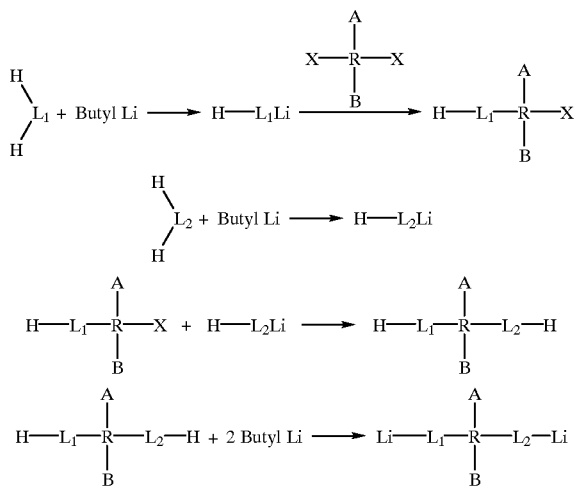

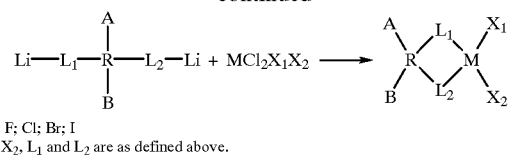

X = F; Cl; Br; I
$X_1$, $X_2$, $L_1$ and $L_2$ are as defined above.

In the case of the unsymmetrical metallocenes, it is also possible to use various substituted or unsubstituted cyclopentadienyl, fluorenyl or amido, phosphido and arsenido radicals as ligands $L_2$, where the substituents of these ligands are as defined for $X_1$ and $X_2$ or else are ferrocenyl- or ruthenocenyl-substituted or -fused.

The invention further provides for the use of the metallocenes of the invention as polymerization catalysts in the polymerization of olefins, and also provides an olefin polymerization process in which the metallocenes of the invention are used as catalysts.

In the olefin polymerization, preference is given to using a cocatalyst, for example an aluminoxane of the formula IV for the linear type:

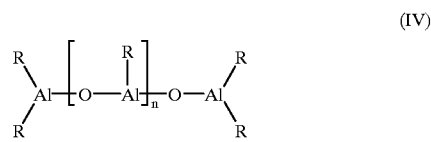  (IV)

and/or the formula V:

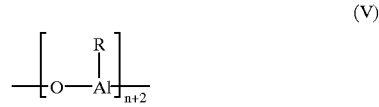  (V)

for the cyclic type, where, in the formulae IV and V, the radicals can be identical or different and are each a $C_1$–$C_6$-alkyl group and n is an integer of 1–50. Preferably, the radicals are identical and are methyl, isobutyl, phenyl or benzyl; particular preference is given to methyl. The aluminoxane can be prepared in various ways by known methods. One possibility is, for example, reacting aluminum alkyls with aluminum sulfate containing water of crystallization (EP 302 424). In the present invention, commercial MAO (methylaluminoxane, from Witco, Germany) is used. It is also possible to mix the metallocene of the formula I with an aluminoxane of the formula IV and/or V before use in the polymerization reaction. The mixing is preferably carried out in solution. Preference is given to dissolving the metallocene in an inert hydrocarbon and subsequently mixing it with the aluminoxane solution. Suitable inert hydrocarbons are aliphatic or aromatic hydrocarbons. Preference is given to using toluene. The concentration of the aluminoxane in the solution is in the range of 5–30% by mass, based on the total solution. The metallocene is preferably used in an amount of $10^{-4}$–1 mol per mol of aluminoxane. The mixing time is from about 5 minutes to 24 hours, preferably from 5 to 60 minutes. Mixing is usually carried out at a temperature of from −10 to +70° C., in particular from 10 to 40° C.

The metallocene can also be applied to a support. Suitable supports are, for example, the inorganic oxides of the metals of main groups II–IV of the Periodic Table. Particular preference is given to catalyst supports as described in EP-A 685 494 and EP-A 787 746.

The polymerization can be carried out in solution, suspension or gas-phase processes, continuously or batchwise at a temperature of from −10 to +200° C., preferably from +20 to +80° C. Olefins of the formula $R^a$—CH=CH—$R^b$ are polymerized or copolymerized. In this formula, $R^a$ and $R^b$ are identical or different and are each a hydrogen atom or an alkyl radical having from 1 to 20 carbon atoms. However, $R^a$ and $R^b$ together with the carbon atoms connecting them can also form a ring. For example, olefins such as ethylene, propylene, 1-butene, 1-hexene, 4-methyl-1-pentene, 1-octene, cyclopentene, norbornene or norbornadiene are polymerized or copolymerized. In particular, ethylene, propylene and 1-butene are polymerized or copolymerized. If necessary, hydrogen is added as molar mass regulator. The total pressure in the polymerization is 0.5–150 bar. Preference is given to carrying out the polymerization in a pressure range of 1–40 bar. It has been found to be advantageous to carry out the reaction of the monomers in the presence of the metallocene catalyst system at a molar ratio of aluminum from the oligomeric aluminoxane compound to the transition metal of the metallocene compound of from $10^6$:1 to $10^1$:1, preferably from $10^4$:1 to $10^2$:1.

If the polymerization is carried out as a suspension or solution polymerization, use is made of an inert solvent. It is possible to use, for example, aliphatic or cycloaliphatic hydrocarbons such as pentane, hexane or cyclohexane. Toluene can also be used. Preference is given to carrying out the polymerization in the liquid monomer.

According to the invention, the copolymerization of ethylene with propylene is carried out in liquid propylene or in hexane as suspension medium. In the polymerization in liquid propylene, the ethylene is preferably introduced in such an amount that a partial pressure ratio $p_{c2}/p_{c3}$ of greater than 0.5, in particular greater than 1.0, is established above the liquid phase ($p_{c2}$=partial pressure of ethylene in the gas phase above the suspension; $p_{c3}$=partial pressure of propylene in the gas phase above the suspension). In the copolymerization in hexane as suspension medium, an ethylene/propylene gas mixture having a propylene content of from 1 to 50 mol %, preferably from 5 to 30 mol %, is fed in. The total pressure is kept constant during the polymerization by metering in further amounts. The total pressure is from 0.5 to 40 bar, preferably from 1 to 20 bar.

The polymerization time is generally from about 10 minutes to 6 hours, preferably from 30 minutes to 2 hours.

The catalysts used according to the invention expand the range of polymerization-active metallocenes for preparing polyolefin homopolymers and copolymers. In particular, the metallocenes of the invention produce polymers and copolymers having a high molar mass and a narrow molar mass distribution in the industrially important temperature range from 20 to 80° C. In the case of known analogous catalysts having the same ligand type, but having a customary bridge, the value for the molar mass is 36,000 g/mol (Chemie in unserer Zeit, 28 (1994), 4, 197–208).

The following examples illustrate the invention.

In the examples:

$M_w$ = weight average molar mass in g/mol,
$M_n$ = number average molar mass in g/mol,
$M_w/M_n$ = molar mass distribution, determined by gel permeation chromatography,
MS = mass spectrometry $^1$H-NMR = $^1$H nuclear magnetic ) 
  resonance spectroscopy ) Elucidation of the
$^{13}$C-NMR = $^{13}$C nuclear magnetic ) catalyst structure
  resonance spectroscopy )

EXAMPLE I 1,1''-[(2-Ferrocenylethyl)methylsilano] diindenylzirconium(IV) dichloride Preparation of [2-(dichloromethylsilyl)ethyl]ferrocene[1] (Dichloro(2-ferrocenylethyl)methylsilane)

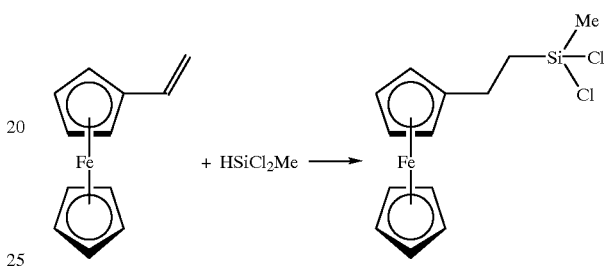

A bomb was charged with vinylferrocene [0.125 g; 0.585 mmol; 1.0 eq]. After addition of 3 drops of $H_2PtCl_6$ (Karstedt catalyst)[2], dichloromethylsilane [0.135 g; 1.17 mmol; 2.0 eq] was subsequently added at −90° C. After thawing, the mixture was heated to 75° C. and stirred at this temperature for 87 hours. After cooling, the excess dichloromethylsilane was taken off in a high vacuum.

[1] Modified hydrosilylation as described by Benkeser et al., J. Org. Chem., Vol 44, No. 9 (1979), 1370 [2] Solution of 45 mg of $H_2PtCl_6$ in 0.9 ml of isopropyl alcohol (Fluka grade for spectroscopy)

Formation of derivatives of dichloro(2-ferrocenylethyl)methylsilane for structure elucidation (a- or b-insertion)

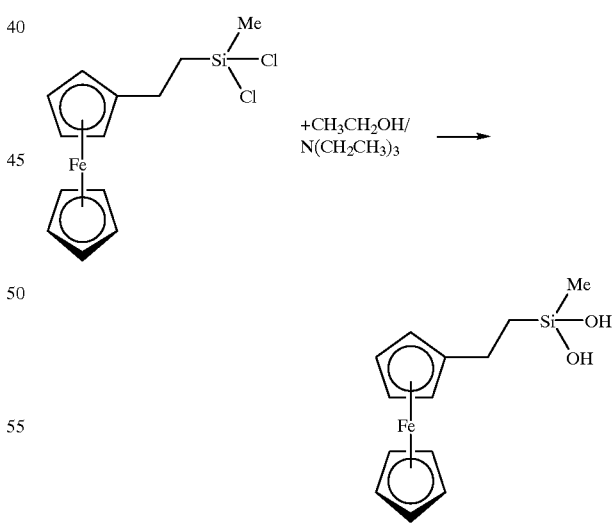

Vinylferrocene [0.418 g; 1.97 mmol; 1.0 eq] and dichloromethylsilane [0.453 g; 3.94 mmol; 2.0 eq] were reacted as described above, but the stirring time at 75° C. was only two hours. The residue remaining after taking off the excess dichloromethylsilane was taken up in 10 ml of absolute ether and admixed with a mixture of absolute ethanol [1 ml; 17 mmol] and absolute triethylamine [2.4 ml; 17 mmol]. The precipitate which was formed immediately was taken up and extracted in 25 ml of ether and 25 ml of water. The remaining ether phase was extracted four times with 25 ml each time of water, twice with 25 ml of half-saturated ammonia chloride solution and once with 25 ml of saturated sodium chloride solution. After drying over Na$_2$SO$_4$ and filtration, the ether was taken off. The product mixture was subjected to flash chromatography: stationary phase: silica gel 60 (Fluka 60738), mobile phase: ether/n-hexane=1:1; cclumn dimensions: 32 cm×2.5 cm.

Owing to the short reaction time, unreacted vinylferrocene was obtained as the main fraction (355 mg); a second fraction (57 mg) which was isolated is, according to the mass spectrum, made up of (2-ferrocenylethyl) ethoxymethylsilanol. The third compound obtained (50 mg of it were isolated) is (2-ferrocenylethyl)methylsilanediol (see reaction scheme):

$^1$H NMR (C$_6$D$_6$, TMS) δ (ppm): 4.51 (broad, —OH)4.10 ("t", subst. cp ring), 4.08 (s, unsubst. cp ring), 3.98 ("t", 2H, subst. cp ring), 2.57 (m, 2H, cp-CH$_2$), 1.06 (m, 2H, Si—CH$_2$), 0.29 (s, 3H, Si—CH$_3$);

IR (Kbr): 3923w, 3188s (broad), 3095s, 2964s, 2917s, 2887s, 2850m, 2362w, 2344w, 2254w, 2053w, 1702s, 1638m, 1470m, 1439m, 1410m, 1395m, 1366w, 1320s, 1260s, 1229m, 1216m, 1164s, 1127s, 1106s, 1044s, 1001s, 845s(broad), 797s, 669s, 644m, 605w, 482s, 418m;

MS (EI, 70 eV): m/z 290.5$^-$ (M+), 289.5 (M+−H) 256.5 (M+−2 OH), 223.5 (M+−H, −cp).

This confirms the b-insertion to form the target intermediate dichloro(2-ferrocenylethyl)methylsilane formed initially.

1,1'-[(2-Ferrocenylethyl)methylsilano] diindenylzirconium dichloride via [2[Di(1H-inden-1-yl)methylsilyl]ethyl]ferrocene

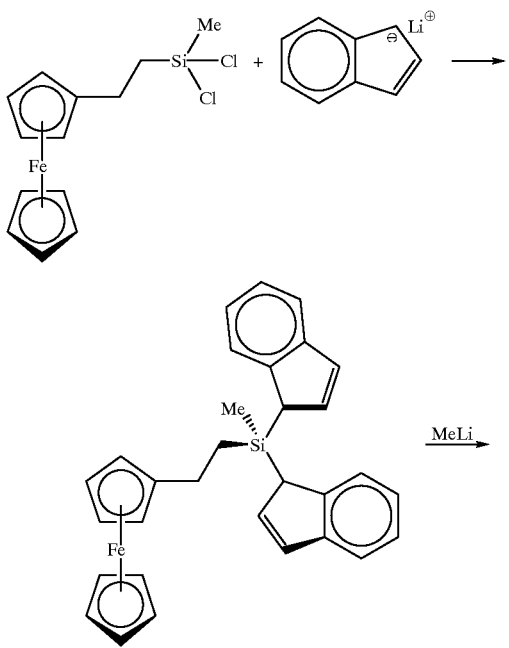

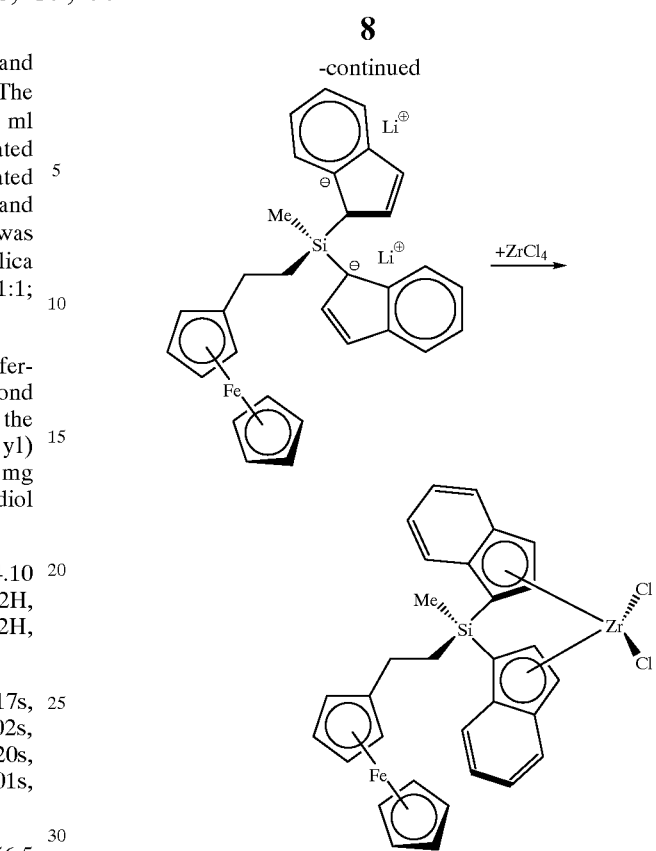

The dichloro(2-ferrocenylethyl)methylsilane prepared as described above [0.667 g; 2.04 mmol; 1.0 eq] was taken up in about 10 ml of absolute THF and added at room temperature to a solution of lithium indenide [0.5 g; 4.09 mmol; 2.0 eq] in 10 ml of absolute THF. After stirring for 18 hours, the solution was treated with two spatula tips of ice and subsequently evaporated to dryness on a Vapsilator. The residue was digested with n-hexane and the hexane solution obtained was subjected to a bed filtration through silica (Fluka 60738).In order to avoid yield losses, the crude product obtained as subjected to no further purification.

Yield (crude product): 0.727 9 of (2-ferrocenylethyl)bis (inden-1-yl)methylsilane (73% based on vinylferrocene used).

The (2-ferrocenylethyl)bis(inden-1-yl)methylsilane obtained [0.727 g; 1.5 mmol; 1.0 eq] was then taken up in 50 ml of absolute ether and admixed at −90° C. while stirring with methyllithium [3.3 mmol; 2.2 eq; 2.1 ml of a 1.6 M solution of MeLi in ether]. After removal of the cooling bath and thawing of the solution, the solution was stirred for another 3 hours, after which 50 ml of absolute n-hexane were added to the previous purely ether solution and the solution was then again cooled to −90° C. The dilithio salt formed was, assuming 100% conversion, admixed with ZrCl$_4$ [0.350g; 1.5 mmol; 1.0 eq]. The cold bath was then removed and the mixture was stirred for another 20 hours at room temperature. The filter cake obtained in the subsequent Schlenk filtration was washed twice with 50 ml each time of a 1:1 mixture of absolute ether and absolute n-hexane. The filtrate containing the product was then evaporated to dryness in a high vacuum and taken up in absolute CH$_2$Cl$_2$. After the solution had been concentrated and cooled to −26° C., a whitish yellow precipitate was formed, and the product remaining in solution was employed for analysis.

Yield (crude product): 540 mg of [(2-ferrocenylethyl)-methylsilanebis(inden-1-yl)]zirconium(IV) dichloride (41% based on vinylferrocene used); $^1$H NMR (CD$_2$Cl$_2$, TMS) δ (ppm): 7.54–6.22 (aromat. H), 4.49–3.83 (H on the ferrocenyl radical), 3.44 (CH$_2$ radicals of unreacted indene[3]), 2.40–2.12 (fec-CH$_2$), 1.46–1.17 (Si—CH$_2$), 0.16 (s, Si—CH$_3$);

$^{13}$C NMR (CD$_2$Cl$_2$, TMS) δ (ppm): 136.2–121.2 (aromat. C), 70.0–65.2 (C of the ferrocenyl radical), 45–15 (multiple signals, fec—CH$_2$ and Si—CH$_2$), 1.2 (Si—CH$_3$).

[3] at 3.3 in indene (Aldrich Library of NMR Spectra, Ed. II, Aldrich Chemical Company, Inc., 1983)

Remark: Due to the many proton signals, it is difficult to quantify the composition of the product (rac/meso ratio). The dominant Si—CH$_3$ singlet signal does, however, indicate the predominant presence of a pseudo-meso form.

Polymerization Example 1

After being made inert, a 2 1 stirred reactor is charged at room temperature with 8.7 g of 30% strength MAO and 300 g of liquid, purified propylene and the mixture is stirred for 15 minutes.

3 mg of 1,1'-[(2-ferrocenylethyl)methylsilano] diindenylzirconium dichloride are dissolved in 1.9 ml of toluene and mixed with 5.8 9 of 30% strength MAO. Subsequently, the catalyst solution together with a further 200 g of propylene are injected into the reactor and the mixture is heated to the polymerization temperature of 70° C. which is kept constant for a period of two hours. The reaction is stopped by flashing off the propylene. 210 g of polypropylene were obtained. 95.8 g of the product were extracted with xylene, giving 82.7 g of an oil (fraction soluble in cold xylene) and 13.1 g of solid polypropylene (fraction insoluble in cold xylene) having a molar mass $M_w$=49,000 and a polydispersity $M_w/M_n$=2.2. The melting point of the solid is 137° C.

What is claimed is:

1. A metallocene of the formula I

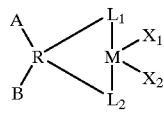

(I)

where M is a metal selected from the group consisting of Ti, Zr, Hf, V, Nb and Ta or an element selected from the group consisting of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, hydrogen or a halogen atom, $L_1$ and $L_2$
a) are identical or different and are each an unsubstituted, monosubstituted or polysubstituted monocyclic or polycyclic hydrocarbon radical containing at least one cyclopentadienyl unit which can form a sandwich structure with M, or
b) $L_1$ is an unsubstituted, monosubstituted or polysubstituted monocyclic or polycyclic hydrocarbon radical containing at least one cyclopentadienyl unit which can form a sandwich structure with M, and $L_2$ is an amido, phosphido or arsenido radical of the formula

where D is nitrogen, phosphorus or arsenic and E is as defined for $X_1$ and $X_2$, R is carbon, silicon, germanium or tin, A and B are identical or different and are ferrocenyl-substituted radicals of the formula

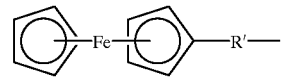

where R' is a $C_1$–$C_{10}$-alkyl group, a $C_6$–$C_{10}$-aryl group, a $C_2$–$C_{10}$-alkenyl group, a $C_7$–$C_{20}$-arylalkyl group, a $C_7$–$C_{20}$-alkylaryl group or a $C_8$–$C_{20}$-arylalkenyl group, where B can also be as defined for $X_1$ or $X_2$.

2. A metallocene as claimed in claim 1, wherin A and B are ferrocenylalkyl radicals.

3. A metallocene as claimed in claim 2, wherein A and B are ferrocenylethyl radicals.

4. A metallocene as claimed in any of claims 1 to 3, wherein the ligands $L_1$ and/or $L_2$ are substituted or unsubstituted cyclopentadienyl, indenyl or fluorenyl radicals.

5. A metallocene as claimed in claim 4, wherein $L_1$ and/or $L_2$ are cyclopentadienyl, tetramethylcyclopentadienyl, indenyl, 2-methylindenyl, 2-methyl-4,5-benzoindenyl, 2-methyl-4-arylindenyl or fluorenyl units.

6. A metallocene as claimed in claim 4, wherein said cyclopentadienyl, indenyl or fluorenyl radicals are substituted by ferrocene or ruthenocene.

7. A process for preparing a metallocene of the formula I as claimed in claim 1, which comprises reacting a compound of the formula II

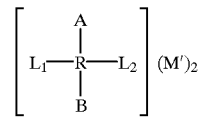

(II)

with a compound of the formula III

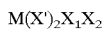

(III)

where $L_1$, $L_2$, A, B, R, M, $X_1$, $X_2$ are as defined in claim 1, M' is an alkali metal and X' is a halogen atom.

8. A process for preparing polyolefins by polymerization of olefins, wherein a metallocene as claimed in claim 1 is used as catalyst.

9. The process for preparing polyolefins as claimed in claim 8, wherein an aluminoxane is used as cocatalyst in addition to the metallocenes.

* * * * *